(12) United States Patent
Bolte

(10) Patent No.: US 7,307,062 B2
(45) Date of Patent: Dec. 11, 2007

(54) METHOD FOR TREATING A MENTAL DISORDER

(76) Inventor: Ellen R. Bolte, 705 Misty Creek Dr., New Lenox, IL (US) 60451

( * ) Notice: Subject to any disclaimer, the term of this patent is extended or adjusted under 35 U.S.C. 154(b) by 296 days.

(21) Appl. No.: 10/741,377

(22) Filed: Dec. 19, 2003

(65) Prior Publication Data

US 2004/0167062 A1    Aug. 26, 2004

(51) Int. Cl.
- *A61K 38/14*    (2006.01)
- *A61K 38/13*    (2006.01)
- *A61K 31/43*    (2006.01)

(52) U.S. Cl. .............. 514/8; 514/11; 514/37; 514/192; 514/200; 530/324; 424/9.1; 424/93.3

(58) Field of Classification Search ........ 514/192, 514/152, 8, 11, 37, 200; 530/324; 536/7.2; 424/93.3, 9.1; 435/170
See application file for complete search history.

(56) References Cited

U.S. PATENT DOCUMENTS

2004/0170617 A1 *   9/2004   Finegold ................. 424/93.45

OTHER PUBLICATIONS

Sandler et al., CID 30, 213-214 (Jan. 2000).*

* cited by examiner

*Primary Examiner*—Chih-Min Kam
(74) *Attorney, Agent, or Firm*—Ruden McClosky; Stanley A. Kim

(57) ABSTRACT

A method of treating an individual exhibiting at least one symptom of a mental disorder is provided which comprises administering to the individual an antimicrobial composition in an amount effective to inhibit or eliminate the at least one symptom of the disorder. This invention also pertains to a method of treating an individual exhibiting at least one symptom of a mental disorder by administering a probiotic mixture to replenish gastrointestinal microbes.

7 Claims, No Drawings

METHOD FOR TREATING A MENTAL DISORDER

RELATED APPLICATIONS

This application claims the benefits of U.S. Provisional Application No. 60/209,712 entitled "Method For Treating Autism" filed on Jun. 5, 2000, U.S. Provisional Application No. 60/214,813 entitled "Therapies for Gastrointestinal and Neurological Disorders" filed on Jun. 28, 2000, and U.S. Provisional Application No. 60/240,582 entitled "Method For Treating Autism—Addition I" filed on Oct. 16, 2000 which are incorporated herein by reference and made a part hereof.

TECHNICAL FIELD

The present invention relates to the therapeutic treatment of mental disorders, and in particular to a new and useful method for treatment of mental disorders by administering an antimicrobial composition and/or administering a probiotic mixture to replenish gastrointestinal microbes.

BACKGROUND OF THE INVENTION

Mental illness is characterized by symptomatic neurological disturbances in a person's thoughts, behaviors, and/or emotions. The term is used to describe a vast array of disorders that affect people of all ages, races, cultures, and socioeconomic classes. Onset may be acute or insidious, and the symptoms may themselves be characterized as ranging from mild to severely disabling.

There is significant comorbidity of mental illness and disturbances of the gastrointestinal tract. Reports indicate that the prevalence rate of gastrointestinal illness is two to three times higher in persons with mental illness than in the normal population. The true level of comorbidity may be far greater than current studies suggest. It has been reported that psychiatric patients do not complain of gastrointestinal symptoms until specifically questioned. One prevailing belief is that the "stress" of coping with a mental illness leads to gastrointestinal disturbances. This diminishes the significance of the gastrointestinal symptoms. Moreover, many of the medications used to treat mental illness may cause gastrointestinal side effects, thus certain symptoms are may wrongly be dismissed as treatment-related.

The gastrointestinal tract is a highly complex ecosystem with as many as 300-400 bacterial species from 30 genera. Typical bacterial counts in the colon are $10^{11-12}$ per gram of feces, and the bacterial composition of multiple specimens collected over time from single individuals appears to be quite stable. Competition for available nutrients and space limits bacterial growth in the colon and contributes to the delicate, yet relatively stable, balance of organisms. This balance is disrupted by the use of broad-spectrum antimicrobials. Large numbers of the intestinal population are killed by broad-spectrum antimicrobial use, substantially diminishing the colonization resistance of the host to deleterious microbes, such as gram-positive, spore-forming anaerobic bacteria. These bacteria are often ubiquitous in nature and are readily found in numerous environments. Approximately 10% of the organisms found in a human stool specimen belong to the *Clostridium* genus. When growth conditions become unfavorable, the bacteria produce spores that tolerate extreme conditions that the vegetative form of the bacteria cannot survive, such as those encountered during antimicrobial treatment.

Published data along several paths may lend credence to the notion that an alteration in gastrointestinal flora contributes to symptoms of mental illness. The first line of evidence is from literature relating to infant botulism. This condition was first recognized as a distinct clinical entity in 1976. It differs from classical botulism in that the intestinal tract becomes colonized by *Clostridium botulinum* and elaboration of the neurotoxin occurs in vivo. Age is a primary risk factor for the development of infant botulism as diagnosis of the disease is rare after 1 year of age. However, the colonization resistance observed in mature animals is greatly diminished when they are treated with broad-spectrum antimicrobials. Similarly, antimicrobial use has been identified as a risk factor for the development of botulism related to intestinal colonization with *C. botulinum* in older children and adults.

The second line of evidence is from human and animal studies which have repeatedly demonstrated that intestinal colonization by opportunistic pathogens such as *Escherichia coli, Klebsiella pneumoniae, Pseudomonas aerguinosa, Salmonella enteritidis, Shigella flexneri*, and *Vibrio cholerae*. Intestinal colonization is greatly enhanced when protective intestinal microbiota are disrupted by broad-spectrum antimicrobials. In humans, the best-documented example of opportunistic colonization of the intestinal tract following antimicrobial use is that by *Clostridium difficile*, the causative agent of pseudomembranous colitis.

Another relevant condition is d-lactic acidosis, in which associated neurological and psychiatric symptoms are well-documented. D-lactic acidosis, a complication of short bowel syndrome or intestinal bypass surgery for obesity, is a condition caused by a change in bacterial flora to an acid-tolerant, aciduric flora. D-lactic acidosis creates a host of behavioral changes such as hostility, slurred speech, stupor, altered mental status, dizziness, asterixis, and ataxia. Treatment is with oral antimicrobials, resulting in rapid cessation of mental signs.

Certain clostridial species produce the most potent neurotoxins known to man. To date, researchers have identified seven serotypes of botulinum neurotoxin (BONT A to G) produced by at least four different clostridial species; *C. botulinum, C. baratii, C. butyricum*, and *C. argentinense*. Thus far, only *C. tetani* is known to produce tetanus neurotoxin (TeTX). The structural genes for clostridial neurotoxin production are chromosomal (BONT type A, B, E, and F), plasmid-associated (TeTX and BONT-G), or bacteriophage-associated (BONT type C, D, and possibly F) DNA. Plasmids and bacteriophages are natural vehicles for the transfer of genetic material between bacteria, including the genes that control neurotoxin production. It is widely accepted and believed that additional clostridial species are capable of neurotoxin production.

Research has demonstrated that tetanus neurotoxin can be transported to the central nervous system (CNS) via retrograde intra-axonal transport along the vagus nerve. Based on this finding, a clostridial neurotoxin, related to TeTX, elaborated by an organism that has colonized the intestinal tract, could gain access to the CNS via retrograde intra-axonal transport along afferent fibers of the vagus nerve. Once the toxin gained access to the CNS, cleavage of synaptic proteins would severely disrupt the delicate balance of neurotransmitters and cause behavioral symptoms indicative of mental illness, as evidenced by laboratory experiments in animals.

Behavioral symptoms have previously been associated with certain infectious diseases. Specific examples of bacteria that may cause psychological symptoms are the causative agent of syphilis, *Treponema pallidum*, and the causative agent of Lyme disease, *Borrelia burgdrferi*. The association of certain gastrointestinal illnesses with neurological and psychological symptoms is also recognized, as in d-lactic acidosis. In spite of the recognized association between bacteria and neurological and psychological symptoms in certain conditions, the possibility that the vast majority of mental illnesses symptoms are caused by a bacterial infection of the intestinal tract is a paradigm shift.

SUMMARY OF THE INVENTION

The present invention provides a method of treating an individual exhibiting at least one symptom of a mental disorder, in particular the method comprises administering to the individual an antimicrobial composition in an amount effective to inhibit or eliminate the at least one symptom of the disorder.

It has been discovered that disruption of the flora within the gastrointestinal tract or poorly developed flora within the gastrointestinal tract of young infants and subsequent pathogenic microbial proliferation in one or more regions of the gastrointestinal tract can mediate a variety of disruptions of neurological functions. Toxins, in particular neurotoxins, produced by one or more species of the proliferating microbes mediate these neurological disruptions.

Administration of broad-spectrum antimicrobials has a profound effect on the normal gastrointestinal flora and can result in colonization with antimicrobial-resistant organisms. In humans, the best-documented example of opportunistic colonization of the intestinal tract following antimicrobial use is that by *Clostridium difficile*, the causative agent of pseudomembranous colitis.

Once the pathogen has become a well-established member of the gastrointestinal flora, elimination may be quite difficult. Any cells remaining after treatment may multiply and result in relapse of psychiatric symptoms. A treatment goal is to create an environment that does not favor the growth of the neurotoxigenic organism(s). Antimicrobials such as vancomycin, metronidazole, bacitracin, teicoplanin, ramoplanin, and fusidic acid have been studied for the treatment of *C. difficile* colitis. When treatment with a single agent failed to result in a remission of symptoms, the use of two antimicrobial agents with different modes of action were used. Particular combinations appear to be synergistic.

It has also been discovered that the present invention, including antibacterial therapy directed to the proliferating microbial species, results in improved mental function through inhibition or elimination of the proliferating species. Furthermore, recurrence of the mental symptoms can be limited or potentially prevented by repopulation of the gastrointestinal tract by normal human gut flora, known as competitive replacement therapy or "probiotic therapy". In all likelihood, the mental syndromes themselves can be prevented or limited in the first place by appropriate probiotic therapy following administration of broad-spectrum antimicrobials.

The pathogenic proliferation of microbes in the gut can at least partially cause deleterious mental symptoms and syndromes of many disorders, including at least some forms of Attention Deficit/Hyperactivity Disorder (ADHD), Autistic Disorder, Childhood Disintegrative Disorder, Conduct Disorder, Oppositional Defiant Disorder, Pervasive Developmental Disorder-Not Otherwise Specified (PDD-NOS), Anxiety Disorder, Mood Disorders including Major Depressive Disorders, Bipolar Disorder (I and II), Psychotic Disorders including Schizophreniform, Schizoaffective Disorder, Schizophrenia (all types), and Psychotic Disorder Not Otherwise Specified. The common etiology of these mental symptoms and syndromes makes possible a common therapeutic and preventative concept, embodied in the present invention.

Although genetic factors are widely heralded as the primary cause of mental illness, not a single gene or chromosomal loci has been conclusively identified as playing a role in the manifestation of any mental illness. Countless laboratory studies have been conducted and hundreds of papers authored, yet the only evidence for a "genetic" etiology remains the increased familial incidence. The role of an infectious microbial agent provides an equally plausible explanation for the increased familial incident rate of mental illness. Thus, a method of treating an individual exhibiting at least one symptom of a mental disorder by administering an antimicrobial composition in an amount effective to inhibit or eliminate the at least one symptom of the disorder, is effective to combat the manifestation of mental disorders.

DETAILED DESCRIPTION

While this invention is susceptible of embodiments in many different forms, there is and will herein be described in detail a preferred embodiment of the invention with the understanding that the present disclosure is to be considered as an exemplification of the principles of the invention and is not intended to limit the broad aspect of the invention to the embodiments illustrated.

The antimicrobials used to treat mental illness caused by intestinal bacteria should have particular characteristics for optimal benefit and minimal side effects. Certain antimicrobials have characteristics appropriate to treat even very young children, and such drugs are useful to treat disorders having the gut-brain involvement. Preferably, an antimicrobial selected as a therapy for any of the above disorders will have one or more of the following properties:

1. In vitro activity against most or all clostridial species;
2. Poor activity against most non-clostridial organisms normally found in the gut flora;
3. Safe doses capable of achieving a concentration in the colon exceeding the minimal inhibitory concentration or minimal bactericidal concentration of the drug by at least four or five two-fold concentrations;
4. Preferably little or no absorption when given orally, minimizing systemic effects;
5. Preferably bactericidal activity;
6. Not cross-resistant with vancomycin or other drugs that are important for treatment of systemic infections;
7. Resistance to the antimicrobial does not develop readily;
8. Palatable in liquid form when taken orally, or readily formulated into other oral doses to enhance patient compliance;
9. Well tolerated orally over extended period of time, preferably at least 3-4 months;
10. Little or no toxicity, either systemically or in the bowel;
11. Preferably effective when given only once or twice daily; and
12. Moderate in price.

Drugs that have one or more of the above characteristics may be utilized for antimicrobial therapy in treating mental disorders with a gut flora etiology. The different modes of action by which antimicrobial agents either kill or inhibit bacterial organisms are elaborated below. The following examples are provided only for the purposes of illustrating the different classes of antibiotics, categorized by their modes of action, and are not intended to limit the scope of the present invention.

Inhibitors of the Cell Wall Synthesis (b-lactams)

The bacterial cell wall is composed of a macromolecular network called peptidoglycan, present either alone or in combination with other substances. Through various mechanisms, certain antibacterial agents prevent the synthesis of intact peptidoglycan. As a consequence of these mechanisms, the cell wall is greatly weakened and results in lysis of the cell. Table 1 below provides a partial listing of these inhibitors.

TABLE 1

Inhibitors of Cell Wall Synthesis

| Class | Specific Examples |
|---|---|
| Natural penicillins | Penicillin V, penicllin G |
| Semisynthetic penicillins | Penicillinase-resistant penicillins (e.g., methicillin, nafcillin, oxacillin, cloxacillin, dicloxacillin), aminopenicillins (e.g., ampicillin, amoxicillin, bacampicillin), carboxypenicillins (carbenicillin, ticarcillin), ureidopenicillins and piperazine penicillin (e.g., azlocillin, mezlocillin, piperacillin), monobactams (e.g., aztreonam, carumonam), carbapenems (e.g., imipenem, meropenem). |
| Cephalosporins | Cephalexin, cefpodoxime proxetil, cefoperazone, cefotaxime, ceftazidime, ceftriaxone, moxalactam, loracarbef, cephradine, cefprozil, cefadroxil, cefamandole, cefoxitin, cefuroxime, cefazolin, cephalothin, RU 59863 |
| Glycopeptides | vancomycin, teicoplanin, teicoplanin A2 complex, ristocetin, aglycone |
| Glycolipodepsipeptide | Ramoplanin |
| Polypeptide | Bacitracin |

Inhibitors of Protein Synthesis

Antibacterial agents in this group can act on the 30S or the 50S portion of the procaryotic ribosome and block protein synthesis. When the bacterial cell cannot produce the proteins it requires as a result of the antibiotic's action, cell death occurs. For example, protein synthesis can be disrupted by inhibiting the binding of tRNA on the 30S or 50S ribosomal subunit, interfering with attachment of tRNA to the mRNA-ribosome complex and thus blocking the growth of the polypeptide chain, or altering the shape of the 30S subunit of the ribosome to result in the incorrect deciphering of genetic code on the mRNA. Table 2 below provides a partial listing of the inhibitors of protein synthesis.

TABLE 2

Inhibitors of Protein Synthesis

| Class | Specific Examples |
|---|---|
| Aminoglycosides | streptomycin, netilmicin, paromomycin, sisomicin, amikacin, neomycin, gentamycin, kanamycin, tobramycin, spectinomycin |
| Tetracyclines | tetracycline, oxytetracycline, chlortetracycline, democlocycline, methacycline, doxycycline, minocycline |
| Macrolides | erythromycin, oleandomycin, triacetyl-oleandomycin (troleandomycin), carbomycin, spiramycin, rosamicin, rosaramicin, azithromycin, josamycin, roxithromycin, clarithromycin, dirithromycin |

TABLE 2-continued

Inhibitors of Protein Synthesis

| Class | Specific Examples |
|---|---|
| Lincosamides | Lincomycin, clinadamycin |
| Streptogramins - group A and group B | Quinupristin/dalfopristin, ostreogrycins, pristinamycins, virginamycins, mikamycins, synergistin A |
| Chloramphenicol | Chloramphenicol, thiamphenicol |
| Ketolides | ABT-773, telithromycin |
| Fusidic Acid | Fusidic acid |
| Everninomycins | Evernimicin (SCH 27899) |
| Oxazolidinones | Linezolid |

Inhibitors of Nucleic Acid Synthesis

These antibacterial agents can be effective due to their action on DNA or RNA synthesis. While the modes of action of the agents in this group may vary, all affect the synthesis of nucleic acids. Particular modes of action include; binding to one subunit of DNA-dependent RNA polymerase and preventing initiation of transcription, inhibiting the activity of DNA gyrase from participating in the coiling and nicking of DNA to form superhelices during replication and transcription, or causing DNA mutations due to a cytotoxic effect. Table 3 below provides a partial listing of the inhibitors of nucleic acid synthesis.

TABLE 3

Inhibitors of Nucleic Acids Synthesis

| Class | Specific Examples |
|---|---|
| Rifamycins | Rifampicin, rifabutin, rifaximin |
| Nitroimidazoles | Metronidazole, tinidazole, ornidazole |
| Quinolones and the fluoroquinolones | nalidixic acid, ciprofloxacin, trovafloxacin, tosufloxacin, sparfloxacin, fleroxacin, pefloxacin, ofloxacin, norfloxacin, levofloxacin |

Inhibitors of Synthesis of Essential Metabolites

Antimicrobial agents that inhibit the synthesis of essential metabolites may compete with microorganisms for required substrate. For example, para-aminobenzoic acid (PABA) is the substrate for an enzymatic reaction leading to the synthesis of folic acid. In the presence of the sulfanilamide, the enzyme that normally converts PABA to folic acid combines with the drug instead, thereby preventing folic acid synthesis. Table 4 below provides a partial listing of the inhibitors of essential metabolites.

TABLE 4

Inhibitors of Synthesis of Essential Metabolites

| Class | Specific Examples |
|---|---|
| Sulfonamides | Sulfamethoxazole |
| 2,4-diaminopyrimidine | Trimethoprim |

Injury to the Plasma Membrane

These agents disrupt the cell membrane by opening membrane channels, resulting in a leakage of metabolites. Other membrane-bound enzyme functions are also inhibited. Table 5 below provides a partial listing of the agents that are injurious to the plasma membrane.

TABLE 5

Injury to the Plasma Membrane

| Class | Specific Examples |
|---|---|
| Polymyxins | Colistin, Polymyxin B |
| Cecropins-magainins | MSI-78 |
| Gramicidin | |
| Polyenes | Amphotericin B (usually fungistatic) |
| Imidazoles | Ketoconazole, miconazole (ususally fungicidal) |

Competitive Replacement Therapy

Competitive replacement therapy may be used alone or in conjunction with antimicrobial therapy. This treatment involves the introduction of nonpathogenic microorganisms ("probiotics") commonly found in the human intestinal tract. These organisms compete with pathogenic organisms for space and available nutrients; thereby inhibiting the growth of bacteria that produce toxins in the intestinal tract. Some of the microbial factors that regulate the gastrointestinal microflora include: production of bacterial metabolites/bacteriocins, influence on host gene expression, substrate depletion, and redox potential. Stability of the flora is achieved when bacteria that derive mutual benefit by association form colonies.

Qualitative and quantitative analysis of stool specimens from four children with autism revealed a complete absence of peptostreptococcal species. Peptostreptococcal species typically account for 10% of the total organism present in the microflora. These children subsequently responded favorably to treatment with vancomycin, but relapsed within two weeks of discontinuance of the antimicrobial therapy. Two of these children were subsequently retreated with antimicrobials and then immediately administered a probiotic fecal enema. Antimicrobial therapy was reinitiated to reduce the numbers of offending bacteria in the intestinal tract. 50 mg of donor stool was collected from a healthy sibling, homogenized with 500 ml of saline and administered as a rectal enema. In both cases, the children's behavior remained substantially improved over baseline for several months after discontinuance of the antimicrobial treatment. Prior to probiotic treatment, regression had consistently occurred within two weeks of ending antimicrobial therapy.

An uncharacterized *Peptostreptococcus* species has been documented to inhibit the growth of clostridia populations in vitro and in animals. The absence of this uncharacterized *Peptostreptococcus* species in certain autistic children may facilitate the growth of clostridial or other toxin-producing bacteria through loss of competitive inhibition. A probiotic taken by mouth would deliver beneficial organisms to all areas of the gastrointestinal tract and may provide a greater benefit.

The ability of "normal flora" to both treat and prevent infection is further supported by the use of probiotics for the treatment of ear infections. It has been reported that children who experience recurrent otitis media infections have streptococci in reduced numbers in their nasopharynx. The benefit of recolonizing the nasopharynx with appropriate organisms was studied. The efficacy of a nasal spray containing five different *Streptococcus* species that are common inhabitants of the nasopharynx was tested in a randomized placebo controlled trial. At three months, 42% of the children given the streptococcal spray were healthy and had a normal tympanic membrane compared with 22% of those given placebo.

The use of a competitive replacement therapy for bowel flora has also been shown to prevent *Salmonella typhimurium* colonization in broiler chicks. A mixed culture composed of 29 bacterial strains representing 10 genera has been described as commonly found in the cecal of adult broiler chicks. Using a continuous-flow culture system, the competitive replacement product was added to the drinking water of newly hatched chicks ($10^8$ anaerobic cfu/ml) and made available for 18 hours. Each chick was estimated to have had an intake of 10 ml of the treated water. Following experimental challenge by *Salmonella typhimurium*, the mean number of these organisms in the cecal contents of treated chicks was significantly decreased as compared to controls.

The probiotic therapy of the present invention is preferably administered as a mixture of a large number of species that are normal, benign inhabitants of the gut, and more preferably in the general proportion in which they are found in healthy humans. A bacterial mixture containing the species *Clostridium innocuum*, *Clostridium ramosum*, *Bacteroides ovatus*, *Bacteroides vulgatus*, *Bacteroides thetaiotamicron*, *Clostridium bifermentans*, *Peptostreptococcus productus*, *Streptococcus faecalis*, and two strains of *Escherichia coli* can be successfully used for the treatment of chronic, relapsing *C. difficile* colitis.

A suitable probiotic mixture is composed of species described as the most prevalent species and in the proportion found normally in the colon. Dosage, measured by colony forming units (cfu) of each bacterium, is preferably at least the number found in the mean count/gram, and is supplied to the patient daily or twice daily for a period of time until it is determined that the bacteria have become established. The formulation can be provided as active cells or spores. It can be provided in an enterically coated form, such as for active cells, to protect sensitive cells from the gastric environment. A preferred therapy involves temporary elimination or suppression of the patient's flora with the use of antimicrobial agents and introduction of a new, non-pathogenic flora that consist of a number of bacteria normally found in the bowel that convey colonization resistance. This therapy is used to prevent regrowth or re-implantation of populations of the offending bacteria.

EXAMPLE 1

Results in Children with Autism, Clinical Trial

Experiments conducted with regressive-onset autistic children have demonstrated success using the present invention. Significant improvement in the symptoms of children with regressive-onset autism has been demonstrated by providing antimicrobials directed toward intestinal bacteria. The terms "regressive-onset," "delayed-onset" or "late-onset" indicate an autistic syndrome that appears in a child generally between 12 and 18 months old who had previously undergone normal development. Symptoms of this syndrome include the loss of language, social, and play skills, and onset of autistic characteristics such as self-stimulation behaviors and the avoidance of eye contact.

Eleven children with regressive onset autism were recruited for an intervention trial using a minimally absorbed oral antibiotic. Entry criteria included antecedent broad-spectrum antimicrobial exposure, followed by chronic persistent diarrhea, deterioration of previously acquired skills, and the subsequent expression of autistic features. Short-term improvement was noted using multiple pre and post-therapy evaluations. These evaluations included coded, paired videotapes scored by a clinical psychologist blinded to treatment status which noted improvement in 8 of 10 children studied.

Institutional human investigation committee approval was obtained for an open-label trial in a narrowly defined subgroup of autistic children. Eleven children (10 males, 1 female; age range: 43-84 months) were enrolled and studied. Inclusion criteria for the study were derived from our central hypothesis and index case characteristics. The criteria included: 1) Meeting diagnostic criteria for Autistic Disorder (DSM IV 299.00); 2) Evaluating and ruling out other genetic and medical diagnoses; 3) Determining a definable, rapid onset after 12 months of age; 4) Antecedent antimicrobial use to the onset of autism symptom(s); 5) Persistent loose stool history, with diarrhea onset before autism symptoms; 6) Symptoms for less than 4 years); 7) Child is between 2-8 years of age; 8) No evidence of any significant medical problem that might complicate treatment such as renal, cardiac or pulmonary disease, severe enterocolitis (visible blood or pus in the stool), or chronic infection, 9) Clinically static for at least 3 months prior to and with no elective changes during the study; and 10) No antimicrobial use for at least 2 months prior to entry into the study. All children had diarrhea and regressive onset of autistic features (occurring at a mean of $17.7\pm3.4$ months) as previously defined in the literature.

A Developmental Profile provided descriptive developmental levels to contrast with developmental age. Although the mean chronological age of the children was $59.4\pm12.7$ months, the mean developmental age for the domains of communication, socialization, and self-help, 23.0 months$\pm$13.0, 25.6 months$\pm$12.9, and $34.4\pm12.4$, respectively, are evidence of their significant developmental delay. The Childhood Autism Rating Scale (CARS) was also administered. Based upon CARS diagnostic categories, six children met the criteria for severe autism, two for moderate autism, and three for mild autism. The antimicrobial dose of vancomycin was 500 mg/day given orally as a liquid (500 mg/6 ml), divided 2 ml t.i.d. for eight weeks. This was followed by four weeks of oral treatment with a probiotic mixture of Lactobacillus acidophilus, L. bulgaricus, and Bifidobacterium bifidum ($40\times10^9$ cfu/ml).

Psychological Evaluations

Two measures of potential improvement were examined. First, children were videotaped for 30 minutes at baseline and once during therapy in a playroom environment. At each session, the child was directed to play with a series of puzzles, books, blocks, and dolls by the mother and then by the evaluator. At the end of the trial, a clinical child psychologist compared coded, paired videotapes of 10 of the 11 children studied. The psychologist viewed each pair of tapes. To diminish the possibility of investigator bias, the tapes were randomly numbered and the psychologist did not have any personal contact with the children. The second measure of potential improvement was the use of behavior and communication analog rating scales the were completed by the study physician at baseline, during therapy, and at follow-up in a manner similar to previously validated methods for other disease states. Results are presented as median scores to account for potential non-linear score increment.

Laboratory Evaluations

Extensive medical evaluations were conducted in parallel with the detailed psychological assessments. Stools were examined for occult blood, inflammatory cells, Aeromonas hydrophila, Cryptosporidium, Clostridium difficile toxin, routine bacterial pathogens, and ova and parasites. Blood tests included complete blood cell counts, chemistry panels, and erythrocyte sedimentation rates. Urinalyses were also obtained. Detailed quantitative aerobic and anaerobic fecal microbiologic studies were conducted at the Wadsworth Anaerobic Bacteriology Laboratory on specimens from four children. Each stool was cultured with a total of 27 different media and atmospheric conditions, modified from standard culturing procedures.

Results

Unblinded assessment using a analog rating scale noted improvement for the group as a whole in communication (Wilcoxon Signed Ranks $Z=-2.9$ $p=0.003$) and behavior (Wilcoxon Signed Ranks $Z=-2.9$, $p=0.003$). To ensure that changes attributed to intervention were not a reflection of differences at baseline, Spearman correlations were conducted. There were no significant correlations between the baseline measure and scores during intervention for either communication (rho=0.35, $p=0.28$) or behavior (rho=0.22, $p=0.51$). Blinded assessment of the coded, paired videotapes noted an improvement during therapy in eight of ten children studied, no change in one, and a possible deterioration in one.

As previously observed in the index case, a brief (1-4 days) period of hyperactivity was noted in six children within three days of initiating antibiotic treatment. One subject then experienced a day of marked lethargy. Otherwise, aside from obvious autistic features, all children had normal physical examinations at baseline and throughout the study, as well as unremarkable basic blood, stool, and urine tests.

Long-Term Follow-Up

Although improvement was clear by several measures, these gains did not endure. One child who had responded significantly to treatment, deteriorated towards the end of the study while still on vancomycin therapy. Data collected during telephone follow-up interviews, conducted weekly during the probiotic therapy, reported substantial behavioral deterioration within two weeks of discontinuance of vancomycin treatment. Due to difficulty in disguising the taste, probiotic treatment compliance was very poor in several children. Behavioral deterioration appeared to occur whether or not the child was compliant with the probiotic therapy regimen. All children were observed in follow-up, ranging from two to eight months after discontinuance of vancomycin. In all but one child, the analog ratings returned towards baseline.

Quantitative Fecal Flora

Stool specimen data from four autistic children prior to vancomycin therapy were compared to those of 104 normal adult subjects from previously published studies (performed under the supervision of the same principal investigator). Anaerobic cocci, chiefly peptostreptococcal species, were present in 93% of the adults' specimens, comprising some 10% of the stool microorganisms. In stark distinction, these species were absent from the stools of each of the four autistic children tested. See the Fecal Flora Table below.

TABLE 6

| | Fecal Flora | | | | |
|---|---|---|---|---|---|
| Organism | Autistic Patient A | Autistic Patient B | Autistic Patient C | Autistic Patient D | Adults (104 Subjects*) |
| Enterobacteriaceae | 6 | 7 | 7 | 7 | 9 |
| Streptococcus | 3 | 5 | 0 | 4 | 9 |
| Enterococcus | 0 | 6 | 0 | 0 | 8 |
| Bacteroides fragilis grp | 8 | 8 | 9 | 8 | 11 |
| Bacteroides, other | 8 | 0 | 9 | 8 | 11 |
| Anaerobic GNR, other | 6 | 4 | 7 | 5 | 8 |
| Peptostreptococcus spp. | 0 | 0 | 0 | 0 | 10† |
| Anaerobic cocci, other | 0‡ | 0 | 0§ | 0 | 11† |
| Lactobacillus spp. | 9 | 9 | 10 | 8 | 10 |
| Bifidobacterium spp. | 7 | 9 | 9 | 8 | 10 |
| Eubacterium spp. | 8 | 0 | 9 | 8 | 11 |
| Clostridium spp. | 9 | 7 | 8 | 8 | 10 |

Units are log10 colony forming units (cfu) gram dry weight
*Mean of positive specimens. Subjects were normal adults on various diets (vegetarian, traditional Japanese diet, or standard Western diet); there were no statistically significant differences in the results between these various groups.
†93% of the 104 subjects had Peptostreptococcus spp. and/or other anaerobic cocci.
‡Ethanol and heat-resistant coccoid forms were present (probably clostridia.)
§Heat-resistant coccoid forms were present (probably clostridia.)

The apparent improvement during treatment with this minimally absorbed antibiotic is not explainable using current conventional genetic hypotheses alone for autism. Results of this preliminary study, along with previous reports of increased intestinal permeability and a "nonspecific colitis" in children with autism, suggests a possible "gut-brain" etiological connection may be present in a subset of these children.

The improvement observed after vancomycin intervention appeared to be significantly greater than could normally be attributable to the characteristic waxing and waning of autistic symptomatology.

A substantial deterioration of the behavioral improvements was reported by most parents within two weeks of ending the vancomycin trial. While the cause for neither the apparent improvement nor the later decline is known, it is possible the deterioration is due to the offending organism being spore-forming, and hence surviving therapy to germinate after vancomycin discontinuation, as has been documented with *Clostridium difficile* infection. An additional possibility is that the therapy was sublethal due to antimicrobial choice and/or dosage regimen permitting emergence of an antimicrobial-resistant bacteria. Since vancomycin is not absorbed, it appears likely that the behavioral improvement was related to the drug's effect on the intestinal tract flora.

The fecal flora of pediatric subjects has been extensively studied. Use of normal adult control fecal specimens in the present study was justified given the documented similarity to pediatric stool flora.

EXAMPLE 2

Case Study

AB was the product of a full-term uncomplicated pregnancy. Development of language, social and play skills proceeded normally until 19 months of age. At that time AB lost expressive and receptive language skills, play skills, self-help skills and his social behavior deteriorated substantially. Immediately prior to the regression, AB had received five 10-day courses of broad-spectrum antimicrobial agents and was taking a "daily maintenance dose" of trimethoprim/sulfamethoxazole as prophylactic therapy. Severe diarrhea, attributed to the antimicrobial therapy, did not improve when the medication was discontinued. He developed abdominal extension, his stools appeared abnormal (foamy, bulky), with undigested food frequently present.

At 25 months of age, a pediatric psychologist diagnosed AB with autistic disorder. Testing at the time included the Vineland Adaptive Behavior Scales; an assessment tool that provides a "normal" age equivalence for developmental achievements in the domains of communication, daily living skills, socialization, and motor skills. AB's composite developmental score was equivalent to an 11 month old (a 14 month developmental delay as compared to chronological age). In spite of extensive laboratory testing, no medical explanation was found for his gastrointestinal symptoms.

At 4 years and 8 months of age, it was decided to begin a 12-week therapeutic trial of vancomycin (125 mg q.i.d.). Immediately prior to beginning treatment with vancomycin, a formal neuropsychiatric evaluation was conducted. Baseline measures included the Vineland Adaptive Behavior Scales and expanded observation by a child psychologist. Although the specific domain scores had changed since the time of AB was diagnosed with autism, his composite developmental score was 11 months. In essence, AB had not achieved any measurable developmental progress since the onset of autism in spite of early intervention.

Three days after initiation of the vancomycin therapy, a hyperactivity pattern emerged which lasted for four days. This was followed by two days of lethargy, and subsequently by a rapid and dramatic clinical improvement. He became affectionate and relatively calm. He promptly achieved toilet training and increased vocabulary. Follow-up neuropsychological evaluation completed after eight weeks of therapy noted an increase in on-task performance, compliance with parental requests, awareness of environmental surroundings, and persistence when engaging in positive activities. A significant reduction in repetitive and self-stimulatory behaviors was also noted. In addition, the composite score for the Vineland Adaptive Behavior Scales increased by 8 months during the first 8-weeks of treatment (i.e., composite score was 19 months). After vancomycin was discontinued, treatment with *Lactobacillus acidophilus, L. bulgaricus*, and *Bifidobacterium bifidum* ($40 \times 10^9$ cfu/ml) was immediately initiated. Shortly after the vancomycin discontinuation, while taking the probiotic agents, behavioral deterioration was observed. The child's educational therapies remained unchanged for both six months before and during the vancomycin trial. Though still improved over baseline, he eventually lost most of the initial gains.

At 5 and a half years of age, a new treatment trial was initiated. AB was treated with metronidazole (250 mg t.i.d.) for 21 days. A child psychologist observed him pre- and post-treatment in his home environment. Baseline behavior was similar to that at the start of the vancomycin trial with the exception of the specific gains that were retained. At the end of metronidazole treatment, aggressive and hyperactive behaviors were substantially reduced. AB began to show increased interest in academic material.

Immediately following the antimicrobial treatment, AB was treated with a probiotic fecal enema in an effort to recolonize his bowel with beneficial organisms. Donor stool for the fecal enema was obtained from AB's healthy 7-year-old sibling. Whole-bowel irrigation with a polyethylene glycol solution (GoLytely™) was used to prepare the bowel prior to the introduction of fifty grams of donor stool suspended in 500 ml of saline. One day later, the probiotic fecal enema was repeated.

Deterioration of behavior had consistently been noted within two weeks of discontinuance of the antimicrobial agent. Following the fecal enema, AB retained all of the gains made during metronidazole treatment and continued to improve daily for an additional two months (while not receiving any other treatments). His behavior remained calm and he was able to focus his attention on learning. For the first time, AB was able to identify all of the basic colors and shapes, identify body parts, match identical items, and imitation of simple gross motor movements. Two months after the fecal enema, he developed explosive diarrhea and experienced a severe behavioral regression in the days that followed. However, as observed in the vancomycin trial, overall gains in cognitive function were retained.

It was then decided to treat AB for a period of not less than six months. A combination of two antimicrobial agents (oral bacitracin at 25,000 units q.i.d. and oral metronidazole at 250 mg t.i.d.) was selected. Each agent has a different purported mechanism of action. Bacitracin, a polypeptide antibiotic, inhibits cell wall synthesis of gram positive organisms. The nitroimidizole, Metronidazole, is incorporated into susceptible anaerobic bacteria where it is metabolized to a cytotoxic product likely disrupting DNA synthesis. Weakening of the bacterial cell wall by the polypeptide bacitracin may increase the nitroimidizole metronidazole absorption by anaerobic bacteria, thus resulting in potentially synergistic activity. Also, by combining the use of metronidazole and bacitracin, risk of developing antimicrobial resistance may be reduced.

A child psychologist completed pre- and post-treatment neuropsychiatric evaluations. Intelligence was difficult to evaluate given the child's severe communication impairment and impulsivity. Baseline behavior was as previously described.

Repeat neuropsychiatric evaluation, completed two months later, again revealed dramatic improvements. Sustained, long-term benefits have been maintained by periodic "cycling" of the antimicrobials (10 days on therapy, followed by 10 days off therapy). After five months of treatment, AB could express his basic needs verbally and had a vocabulary of >100 meaningful words. He played with a wide range of computer software programs, enjoys coloring pictures, and played appropriately with "toddler" toys. AB spent most of his time engaged in positive, playful activities. Aggressive outburst were completely extinguished. AB was able to identify by sight (and sound) all of letters in the alphabet, spell simple words and was beginning to sight-read. He demonstrated proficiency in number recognition and could answer simple addition problems. An. evaluation completed by school district professionals (after six months of treatment) reported that AB's "reading readiness" skills are at a 5.5 year old level and math skills are at a 5.0 year old level (AB's age at the time of testing was 7.0).

After nine months of treatment, AB was forming short sentences 3-4 word without prompting. AB made such dramatic gains in academics and language that district personnel changed the school placement to a learning-disabled classroom at the local public school. AB had previously attended class at a private school for children with severe disabilities. At this point, antimicrobial therapy was discontinued and probiotic treatment with *Lactobacillus* GG was initiated. *Lactobacillus* GG was selected on the basis of its purported efficacy in the treatment of other gastrointestinal illnesses. As observed when the vancomycin was discontinued, a severe deterioration in behavior occurred within two weeks (while AB was taking the probiotic agent). Stereotyped movements, aggressive behavior and an irritable disposition were prominent. Gains in expressive language were retained. Cognitive gains appeared intact, although testing was difficult due to the child's inability to concentrate and uncooperative disposition.

Another treatment trial was conducted when AB was 8 years old. At that time, the most problematic behaviors were aggression towards others and extreme irritability. Based upon previous treatment successes and failures, it was believed that long-term benefit depended upon the adequate elimination and/or suppression of clostridial spores. The ability of bacterial spores to survive antimicrobial treatment and germinate following the discontinuance of the medication is a well-documented phenomenon, as evidenced by chronic, relapsing *C. difficile* infection. Therefore, it was decided to design a tapered dosing schedule for the antimicrobial agents on the basis that slowly decreasing the dose would allow the "normal" bowel flora to stabilize while continuing to suppress the pathogenic organisms. Treatment began, as before, with three weeks of therapy with metronidazole (250 mg t.i.d.) and oral bacitracin (25,000 units q.i.d.). Then, the agents were tapered as follows:

One week of metronidazole 250 mg b.i.d., bacitracin 25,000 units t.i.d.

One week of metronidazole 250 mg once a day, bacitracin 25,000 units once a day.

Ten days of above dosage given every other day.

Significant improvement in behavior and enhanced cognitive functioning were maintained for five months after treatment was completed. During this time, AB made dramatic cognitive gains including, counting money, telling time, and understanding the calendar. Thereafter, AB experienced a behavioral regression but remained substantially improved over baseline.

Shortly thereafter, treatment for AB was reinitiated. Metronidazole and bacitracin were administered for six weeks at the above-mentioned dosages. After a positive clinical response was shown, polymyxin B (1.5 million units t.i.d.) and nystatin (100,000 units t.i.d.) were added to the treatment regimen. Polymyxin B, an antibiotic that damages the plasma membrane, and nystatin, an antifungal agent, were administered for seven days. Thereafter, whole-bowel irrigation with 2,800 ml of polyethylene glycol solution (GoLytely™) was used to prepare AB's intestinal tract for the infusion of replacement bacteria. In the absence of a suitable commercial product, a bacterial mixture was prepared from fresh stool that was collected from AB's healthy sibling. Ten grams of stool was mixed into 500 ml of fluid. The fluid consisted of a mixture of 250 ml of water and 250 ml of no-fat milk, and was preheated to 99° F. The mixture was strained and administered via nasogastric tubing into the stomach for passage throughout the small bowel. Immediately thereafter, 20 grams of stool was mixed into another 500 ml of the fluid mixture and given as a retention enema. This treatment resulted in significant and ongoing gains in social development.

EXAMPLE 3

Case Study

CC was a fourteen year old male whose symptoms were consistent with major depressive disorder, obsessive compulsive disorder, and atypical psychosis. Standard antipsychotic medications were unsuccessful in treating the symptoms. CC also had severe gastrointestinal symptoms and was subsequently diagnosed with Crohn's disease. CC began treatment with prednisone and mesalamine, a standard therapy for Crohn's disease. Treatment with metronidazole (250 mg t.i.d.) was ordered simultaneously and continued for six weeks. CC showed a rapid improvement in attitude, mood and rebounded academically. Behavior problems were absent. A subsequent deterioration in behavior was first noted two months following the discontinuance of the metronidazole. A few months thereafter, CC experienced an acute psychiatric relapse and was admitted to the hospital. A colonoscopy confirmed active lesions in the right colon consistent with Crohn's disease. Treatment with prednisone and mesalamine was initiated for his Crohn's disease, with the prednisone later tapered to 20 mg/day after several months. Although his subtle gastrointestinal symptoms resolved, his psychotic features failed to improve despite further trials of anti-psychotic agents. Three months after the psychiatric relapse, a second course of metronidazole (500 mg t.i.d. for 30 days) was initiated. Within three weeks, a dramatic improvement in his psychiatric symptoms was again noted, and by five weeks he was off all anti-psychotic medication. CC was able to return to high school and completed his junior year with high honors.

EXAMPLE 4

Case Study

Diagnosis: Attention deficit/hyperactivity disorder (at age 7), Major depressive disorder (at age 13), Bipolar (at age 14). Other diagnoses for which DSM-IV criteria are met include: Conduct Disorder S.H. was the product of a full-term uncomplicated pregnancy. Childhood development was normal until 18 months of age. At that time, S.H. developed chronic ear infections. S.H. was repeatedly treated with broad-spectrum antimicrobials and twice had surgery for the placement of ear tubes. She began speech therapy at 4 and a half years old. Early history is also notable for diarrhea, vomiting, body aches, hypersensitivity to sound, and insomnia. At 7 years old, she was diagnosed with attention deficit/hyperactivity disorder and counseling was undertaken. At 10 years of age, S.H. began to threaten suicide. At 13 years of age, S.H. became obsessive and was diagnosed with Major Depressive Disorder and prescribed paroxetine. Six months later, the diagnosis was changed to Bipolar II Disorder and S.H. was admitted to a treatment facility. Treatment with gabapentin was initiated and she was subsequently released.

During the fall of S.H.'s freshman year of high school, her symptoms dramatically escalated. Treatment with gabapentin and paroxetine was discontinued and S.H. was prescribed valproic acid and venlafaxine. Initially, these medications appeared to help slightly, but the improvement quickly waned.

It was decided to begin a 30-day therapeutic trial of metronidazole (500 mg b.i.d.). During the first week of treatment, S.H. became highly agitated. After two weeks of treatment, her thought process became considerably clearer. She could be reasoned with and began to pay attention. A significant reduction in aggression/tempter outbursts, impulsivity, and odd behavior were noted during the final weeks of treatment. Two weeks after mentronidazole therapy was discontinued, S.H.'s behavior deteriorated. She became irritated and very moody. S.H. herself noticed the difference and requested treatment with metronidazole be resumed. After one month of treatment, the difference was astounding. S.H. began attending class regularly. She became respectful of others and was no longer physically aggressive towards her siblings. She has resumed proper care of her personal hygiene. Prior to metronidazole treatment, S.H. had a number of behavior problems that were considered severe in degree including odd, bizarre behavior, impulsivity, aggressive behavior, disobedience, irritable, temper outbursts, stereotyped movements, and sudden mood changes. After two months of treatment, all of these behavior problems were rated as slight in degree or completely resolved.

EXAMPLE 5

Case History

DSM-IV Diagnosis: Autistic Disorder

CM was born prematurely at 28 weeks gestation weighing 2 pounds, 10 ounces. He remained hospitalized for 80 days and suffered from significant medical complications due to his premature birth. CM has been diagnosed with spastic quadriplegia with moderately impaired neuromotor and cognitive functioning. He has severe delays in fine and gross motor skills. Also, severe delays in receptive and expressive language, consistent with his premature birth.

CM was making progress before developmental and behavioral regression occurred. CM had started to say words such as mama, dada, baba, up. CM lost expressive language skills and began to exhibit numerous negative behaviors consistent with an autistic spectrum disorder. Specific behaviors include irritability and temper tantrums, odd meaningless movements, and odd meaningless vocalizations. CM also exhibited difficulty in social situations and showed little interest in playing with peers or forming relationships with his peers.

CM had frequent ear infections and was placed on a six-month "maintenance dose" of trimethoprim/sulfamethoxazole as prophylactic therapy. In spite of the placement of tympanostomy tubes at 18 months of age, CM continued to develop recurrent and persistent otis media untila second set of tubes were inserted approximately six months later.

Recently, CM, now 5 years old, was treated with clarithromycin. According to parental report, CM became more cooperative and was much calmer. CM was happier and showed more interest in things going on around him. Head banging and tantrums stopped.

EXAMPLE 6

Case History

DSM-IV Diagnosis: Childhood Disintegrative Disorder

N.D. was the product of a full term uncomplicated pregnancy. He met all the major developmental milestones within normal age limits and began using his first words when he was 17 months old. Shortly after N.D.'s third birthday, he began to show abnormal behavior patterns: temper tantrums, self-injury, aggression towards others, oppositional, and echolalia, just to name a few. After seeing many specialists throughout the year, he was finally diagnosed with autism January 2000, shortly after his fourth birthday.

At age 4 years 9 months, N.D. was treated with metronidazole (standard dosage for his age/weight,) for 17 days, followed by *Lactobacillus Acidophilus* GG, (Culturelle), 20 billion cells per day. Table 7 below summarizes N.D.'s experience during metronidazole therapy and the resultant behavior deterioration shortly after discontinuation.

TABLE 7

| Classification | Baseline Behavior/Before Metronidazole | During Metronidazole | After Metronidazole |
|---|---|---|---|
| Attitude/State of Mind | Easily frustrated | More in control and easy going about things | Reverted to baseline behavior |
| Attitude/State of Mind | Grumpy | Happy, pleasant | Reverted to baseline behavior |
| Attitude/State of Mind | Not in touch with his environment | Aware of surroundings and others | Reverted to baseline behavior |
| Attitude/State of Mind | Depressed, negative, irritable | Balanced, at ease and happy in his frame of mind and approach to life | Reverted to baseline behavior |
| Attitude/State of Mind | Hyperactive | Relaxed and calm | Reverted to baseline behavior |
| Social behavior | Inflexible, oppositional | Compliant and obedient, more willing to learn | Reverted to baseline behavior |
| Social behavior | Completely non affectionate | Gave hugs at bedtime | Reverted to baseline behavior |
| Social behavior | Poor peer interaction and play skills | Marked improvement in peer interaction and play skills | Reverted to baseline behavior |
| Social behavior | Needed to be in control of everything | Flexible and open to others' ideas and alternatives | Reverted to baseline behavior |
| Social behavior | Aggressive towards little brother | No aggression towards little brother, played very well | Reverted to baseline behavior |
| Speech | Voice quality bombastic, loud, and monotone | Voice normal, natural, with normal inflections | Reverted to baseline behavior |
| Speech | Social communication nearly nonexistent | Initiated and maintained conversation with anyone, family or stranger. Waved to the bus driver-never did that before | Reverted to baseline behavior |
| Speech | Speech often illogical, nonsensical, and disjointed | Speech on topic, more expressive | Initially regressed, improved with speech therapy |
| Ability: Physical or Mental | Poor sleeper | Fell asleep quickly from first day | Remained somewhat improved over baseline |
| Ability: Physical or Mental | Would whine or cry whenever he required help with a task | Could verbalize his need for help | Reverted to baseline behavior |
| Ability: Physical or Mental | Whines and cries often when he needed food or drink | Used appropriate language to express his needs/wants | Reverted to baseline behavior |
| Ability: Physical or Mental | Could not help himself, would fall apart when things were too difficult | Showed signs of problem solving, thinking things through | Reverted to baseline behavior |

TABLE 7-continued

| Classification | Baseline Behavior/Before Metronidazole | During Metronidazole | After Metronidazole |
|---|---|---|---|
| Ability: Physical or Mental | Hyper-sensitive to pain-cried extremely with any sight injury | Easily brushed off any falls or bumps without so much a whimper | Reverted to baseline behavior |
| Ability: Physical or Mental | Resistant to try new foods, very limited diet | Day 14 asked for a hard-boiled egg. Never had one before | Somewhat improved over baseline |

Within a week after the discontinuation of metronidazole, many of the positive gains noted during the treatment began to deteriorate.

EXAMPLE 7

Case History

DSM IV Diagnosis—Autistic Disorder

K.H. is the product of a normal, healthy pregnancy. By 15 months of age, K.H. was beginning two word combinations, enjoyed playing with his brother and demonstrated joint attention skills. In all respects, development appeared to be completely normal. K.H. experienced an unexplainable regression in behavior and language development. By 20 months of age, K.H. could no longer speak a single word and by 24 months of age he lost receptive language skills, eye contact and play skills. He experienced difficulty sleeping at night and experienced "night terrors."

K.H., currently 10 years old, is non-verbal, extremely hyperactive, with widely varying mood states. K.H. has had reoccurring ear infections since the age of 18 months. Most recently, when K.H. experiences an ear infection, he is prescribed either cefpodoxime proxetil, a cephalosporin, and/or an amoxicillin with a beta-lactamase inhibitor, such as clavulanate potassium. K.H. experiences positive improvement in his autistic symptoms when taking these antimicrobials. Noted improvements include, calmness, improved sleep patterns, and the use of more signs for communication. As soon as K.H.'s antibiotics were finished, K.H. became more hyper, more easily aggitated, and more aggressive.

It is understood that, given the above description of the embodiments of the invention, various modifications may be made by one skilled in the art. Such modifications are intended to be encompassed by the claims below.

I claim:

1. A method for treating an individual exhibiting symptoms of autistic disorder, the method comprising the steps of:
    (a) identifying at least one symptom exhibited by the individual indicative of the autistic disorder;
    (b) administering at least one antimicrobial agent to said individual in an amount effective to reduce or eliminate said at least one symptom of said autistic disorder, the antimicrobial agent selected from the group consisting of: vancomycin, metronidazole, bacitracin, and polymyxin B
    wherein the antimicrobial agent is effective against at least one microorganism within the gastrointestinal tract of said individual; and
    (c) administering to said individual a probiotic mixture of *Lactobacillus acidophilus, Lactobacillus bulgaris*, and *Bifidobacterium bifidum* in an amount effective to replenish microorganism levels in the gastrointestinal tract of said individual.

2. The method of claim 1, wherein step (b) of administering at least one antimicrobial agent to the individual comprises administering to the individual at least two antimicrobial agents selected from the group consisting of: vancomycin, metronidazole, bacitracin, and polymyxin B.

3. The method of claim 1, wherein the at least one microorganism within the gastrointestinal tract of said individual is a species of *Clostridium* selected from the group consisting of *Clostridium difficile* and *Clostridium tetani*.

4. The method of claim 1, wherein the antimicrobial agent is vancomycin and the amount effective to reduce or eliminate said at least one symptom of said autistic disorder is about 500 mg per day.

5. The method of claim 1, wherein the antimicrobial agent is metronidazole and the amount effective to reduce or eliminate said at least one symptom of said autistic disorder is in the range of about 250 mg per day to about 750 mg per day.

6. The method of claim 1, wherein the at least one antimicrobial agent is bacitracin and the amount effective to reduce or eliminate said at least one symptom of said autistic disorder is in the range of about 25,000 units per day to about 100,000 units per day.

7. The method of claim 1, wherein the at least one antimicrobial agent is polymyxin B and the amount effective to reduce or eliminate said at least one symptom of said autistic disorder is about 4.5 million units per day.

* * * * *

UNITED STATES PATENT AND TRADEMARK OFFICE
CERTIFICATE OF CORRECTION

| | | |
|---|---|---|
| PATENT NO. | : 7,307,062 B2 | Page 1 of 1 |
| APPLICATION NO. | : 10/741377 | |
| DATED | : December 11, 2007 | |
| INVENTOR(S) | : Ellen R. Bolte | |

It is certified that error appears in the above-identified patent and that said Letters Patent is hereby corrected as shown below:

Title Page, add the following:

'Related U.S. Application Data'
(63) Continuation of application No. 09/866,033, filed on May 25, 2001, now abandoned.

(60) Provisional application No. 60/209,712, filed on June 5, 2000; Provisional application No. 60/214,813, filed on June 28, 2000; and Provisional application No. 60/240,582, filed on October 16, 2000.

In the specification, column 1, lines 1-14, should read as follows:

CROSS-REFERENCE TO RELATED APPLICATIONS

The application claims the benefits of United States Nonprovisional Patent Application Serial No. 09/866,033 entitled "Method for Treating a Mental Disorder," filed on May 25, 2001, now abandoned, which claims priority to Provisional Application No. 60/209,712 entitled "Method for Treating Autism," filed on Jun. 5, 2000, United States Provisional Application No. 60/214,813 entitled "Therapies for Gastrointestinal and Neurological Disorders," filed on Jun. 28, 2000, and United States Provisional Application No. 60/240,582 entitled "Method For Treating Autism-Additional 1," filed on Oct. 16, 2000 which are incorporated herein by reference and made a part hereof.

Signed and Sealed this

Twenty Second Day of April, 2008

JON W. DUDAS
*Director of the United States Patent and Trademark Office*